(12) United States Patent
Aravalli

(10) Patent No.: US 11,324,507 B2
(45) Date of Patent: May 10, 2022

(54) DEVICE AND METHOD FOR ATTACHMENT OF A STOMAL SLEEVE

(71) Applicant: Covidien LP, Mansfield, MA (US)

(72) Inventor: AVVLN Srinivasa Murthy Aravalli, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 431 days.

(21) Appl. No.: 16/162,039

(22) Filed: Oct. 16, 2018

(65) Prior Publication Data

US 2019/0133588 A1 May 9, 2019

Related U.S. Application Data

(60) Provisional application No. 62/581,059, filed on Nov. 3, 2017.

(51) Int. Cl.
*A61B 17/115* (2006.01)
*A61B 17/11* (2006.01)
(Continued)

(52) U.S. Cl.
CPC ....... *A61B 17/1155* (2013.01); *A61B 17/1114* (2013.01); *A61F 5/445* (2013.01);
(Continued)

(58) Field of Classification Search
CPC ............. A61B 17/1155; A61B 17/1114; A61B 17/07292; A61B 17/17257;
(Continued)

(56) References Cited

U.S. PATENT DOCUMENTS 3,193,165 A   7/1965 Akhalaya et al.
3,388,847 A   6/1968 Kasulin et al.
(Continued)

FOREIGN PATENT DOCUMENTS

CA   908529 A    8/1972
CA   2805365 A1  8/2013
(Continued)

OTHER PUBLICATIONS

European Search Report dated Apr. 10, 2019, issued in EP Appln. No. 18204173.

*Primary Examiner* — Chelsea E Stinson
*Assistant Examiner* — Scott A Howell

(57) ABSTRACT

The presently disclosed stapling device includes a stomal sleeve secured to an anvil assembly of a tool assembly of the stapling device. The stomal sleeve has a tubular configuration having a first end portion secured to a tissue contact surface of the anvil assembly and a second end portion secured to a distal face of an anvil head of the anvil assembly. In use, the stapling device is fired to secure the first end portion of the stomal sleeve to dermal and intestinal tissue within a stoma and to separate the first end portion of the stomal sleeve from the anvil assembly. When the stapling device is withdrawn from the stoma, the second end portion of the stomal sleeve is withdrawn from the stoma and subsequently disengaged from the anvil head of the anvil assembly such that the second end portion of the stomal sleeve is positioned externally of the stoma.

7 Claims, 8 Drawing Sheets

(51) Int. Cl.
*A61F 5/445* (2006.01)
*A61B 17/072* (2006.01)
*A61B 17/00* (2006.01)

(52) U.S. Cl.
CPC .................. *A61B 17/07292* (2013.01); *A61B 2017/00004* (2013.01); *A61B 2017/07257* (2013.01); *A61B 2017/1132* (2013.01)

(58) Field of Classification Search
CPC .. A61B 2017/17257; A61B 2017/1132; A61B 2017/00336; A61B 2017/3435; A61B 5/4238; A61B 5/6871; A61B 2018/00494; A61B 1/00135; A61B 2017/00004; A61B 2017/07257; A61F 5/445
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |

(56) References Cited

U.S. PATENT DOCUMENTS

| | | | |
|---|---|---|---|
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,439,446 B1 | 8/2002 | Perry et al. | |
| 6,443,973 B1 | 9/2002 | Whitman | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,257 B2 * | 1/2003 | Grant | A61B 17/07207 606/151 |
| 6,503,259 B2 | 1/2003 | Huxel et al. | |
| 6,517,566 B1 | 2/2003 | Hovland et al. | |
| 6,520,398 B2 | 2/2003 | Nicolo | |
| 6,533,157 B1 | 3/2003 | Whitman | |
| 6,551,334 B2 | 4/2003 | Blatter et al. | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,601,749 B2 | 8/2003 | Sullivan et al. | |
| 6,605,078 B2 | 8/2003 | Adams | |
| 6,605,098 B2 | 8/2003 | Nobis et al. | |
| 6,626,921 B2 | 9/2003 | Blatter et al. | |
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,652,542 B2 | 11/2003 | Blatter et al. | |
| 6,656,193 B2 * | 12/2003 | Grant | A61B 17/072 606/151 |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |
| 6,695,199 B2 | 2/2004 | Whitman | |
| 6,698,643 B2 | 3/2004 | Whitman | |
| 6,716,222 B2 | 4/2004 | McAlister et al. | |
| 6,716,233 B1 | 4/2004 | Whitman | |
| 6,726,697 B2 | 4/2004 | Nicholas et al. | |
| 6,742,692 B2 | 6/2004 | Hartwick | |
| 6,743,244 B2 | 6/2004 | Blatter et al. | |
| 6,763,993 B2 | 7/2004 | Bolduc et al. | |
| 6,769,590 B2 | 8/2004 | Vresh et al. | |
| 6,769,594 B2 | 8/2004 | Orban, III | |
| 6,820,791 B2 | 11/2004 | Adams | |
| 6,821,282 B2 | 11/2004 | Perry et al. | |
| 6,827,246 B2 | 12/2004 | Sullivan et al. | |
| 6,840,423 B2 | 1/2005 | Adams et al. | |
| 6,843,403 B2 | 1/2005 | Whitman | |
| 6,846,308 B2 | 1/2005 | Whitman et al. | |
| 6,852,122 B2 | 2/2005 | Rush | |
| 6,866,178 B2 | 3/2005 | Adams et al. | |
| 6,872,214 B2 | 3/2005 | Sonnenschein et al. | |
| 6,874,669 B2 | 4/2005 | Adams et al. | |
| 6,884,250 B2 | 4/2005 | Monassevitch et al. | |
| 6,905,504 B1 | 6/2005 | Vargas | |
| 6,938,814 B2 | 9/2005 | Sharma et al. | |
| 6,942,675 B1 | 9/2005 | Vargas | |
| 6,945,444 B2 | 9/2005 | Gresham et al. | |
| 6,953,138 B1 | 10/2005 | Dworak et al. | |
| 6,957,758 B2 | 10/2005 | Aranyi | |
| 6,959,851 B2 | 11/2005 | Heinrich | |
| 6,978,922 B2 | 12/2005 | Bilotti et al. | |
| 6,981,941 B2 | 1/2006 | Whitman et al. | |
| 6,981,979 B2 | 1/2006 | Nicolo | |
| 7,032,798 B2 | 4/2006 | Whitman et al. | |
| 7,059,331 B2 | 6/2006 | Adams et al. | |
| 7,059,510 B2 | 6/2006 | Orban, III | |
| 7,077,856 B2 | 7/2006 | Whitman | |
| 7,080,769 B2 | 7/2006 | Vresh et al. | |
| 7,086,267 B2 | 8/2006 | Dworak et al. | |
| 7,114,642 B2 | 10/2006 | Whitman | |
| 7,118,528 B1 | 10/2006 | Piskun | |
| 7,122,044 B2 | 10/2006 | Bolduc et al. | |
| 7,128,748 B2 * | 10/2006 | Mooradian | A61B 17/115 606/151 |
| 7,141,055 B2 | 11/2006 | Abrams et al. | |
| 7,168,604 B2 | 1/2007 | Milliman et al. | |
| 7,179,267 B2 | 2/2007 | Nolan et al. | |
| 7,182,239 B1 | 2/2007 | Myers | |
| 7,195,142 B2 | 3/2007 | Orban, III | |
| 7,207,168 B2 | 4/2007 | Doepker et al. | |
| 7,220,237 B2 | 5/2007 | Gannoe et al. | |
| 7,234,624 B2 | 6/2007 | Gresham et al. | |
| 7,235,089 B1 | 6/2007 | McGuckin, Jr. | |
| RE39,841 E | 9/2007 | Bilotti et al. | |
| 7,285,125 B2 | 10/2007 | Viola | |
| 7,303,106 B2 | 12/2007 | Milliman et al. | |
| 7,303,107 B2 | 12/2007 | Milliman et al. | |
| 7,309,341 B2 | 12/2007 | Ortiz et al. | |
| 7,322,994 B2 | 1/2008 | Nicholas et al. | |
| 7,325,713 B2 | 2/2008 | Aranyi | |
| 7,334,718 B2 | 2/2008 | McAlister et al. | |
| 7,335,212 B2 | 2/2008 | Edoga et al. | |
| 7,364,060 B2 | 4/2008 | Milliman | |
| 7,398,908 B2 | 7/2008 | Holsten et al. | |
| 7,399,305 B2 | 7/2008 | Csiky et al. | |
| 7,401,721 B2 | 7/2008 | Holsten et al. | |
| 7,401,722 B2 | 7/2008 | Hur | |
| 7,407,075 B2 | 8/2008 | Holsten et al. | |
| 7,410,086 B2 | 8/2008 | Ortiz et al. | |
| 7,422,137 B2 | 9/2008 | Manzo | |
| 7,422,138 B2 | 9/2008 | Bilotti et al. | |
| 7,431,191 B2 | 10/2008 | Milliman | |
| 7,438,718 B2 | 10/2008 | Milliman et al. | |
| 7,455,676 B2 | 11/2008 | Holsten et al. | |
| 7,455,682 B2 | 11/2008 | Viola | |
| 7,481,347 B2 | 1/2009 | Roy | |
| 7,494,038 B2 | 2/2009 | Milliman | |
| 7,506,791 B2 | 3/2009 | Omaits et al. | |
| 7,516,877 B2 | 4/2009 | Aranyi | |
| 7,527,185 B2 | 5/2009 | Harari et al. | |
| 7,537,602 B2 | 5/2009 | Whitman | |
| 7,540,839 B2 | 6/2009 | Butler et al. | |
| 7,546,939 B2 | 6/2009 | Adams et al. | |
| 7,546,940 B2 | 6/2009 | Milliman et al. | |
| 7,547,312 B2 * | 6/2009 | Bauman | A61B 17/072 227/175.1 |
| 7,556,186 B2 | 7/2009 | Milliman | |
| 7,559,451 B2 | 7/2009 | Sharma et al. | |
| 7,585,306 B2 | 9/2009 | Abbott et al. | |
| 7,588,174 B2 | 9/2009 | Holsten et al. | |
| 7,600,663 B2 | 10/2009 | Green | |
| 7,611,038 B2 | 11/2009 | Racenet et al. | |
| 7,635,385 B2 | 12/2009 | Milliman et al. | |
| 7,669,747 B2 | 3/2010 | Weisenburgh, II et al. | |
| 7,686,201 B2 | 3/2010 | Csiky | |
| 7,694,864 B2 | 4/2010 | Okada et al. | |
| 7,699,204 B2 | 4/2010 | Viola | |

(56) References Cited

U.S. PATENT DOCUMENTS

| | | |
|---|---|---|
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 * | 9/2011 | Bettuchi .......... A61B 17/07292 227/176.1 |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,381,729 B2 * | 2/2013 | Freitag .................. A61M 16/16 128/207.14 |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 * | 6/2013 | Bettuchi .......... A61B 17/07207 227/176.1 |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,237,892 B2 * | 1/2016 | Hodgkinson .... A61B 17/07207 |
| 9,272,406 B2 * | 3/2016 | Aronhalt .......... A61B 17/07207 |
| 9,980,727 B2 * | 5/2018 | Khosrovaninejad ........................ A61F 5/0013 |
| 2003/0111507 A1 | 6/2003 | Nunez |
| 2004/0073090 A1 | 4/2004 | Butler et al. |
| 2005/0010297 A1 * | 1/2005 | Watson ................ A61F 2/442 623/17.12 |
| 2005/0051597 A1 | 3/2005 | Toledano |
| 2005/0107813 A1 | 5/2005 | Gilete Garcia |
| 2005/0149173 A1 * | 7/2005 | Hunter .................. A61B 17/11 623/1.42 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0118157 A1 * | 5/2007 | Zuidema ................ A61B 46/30 606/153 |

(56) References Cited

U.S. PATENT DOCUMENTS

| | | |
|---|---|---|
| 2008/0135044 A1* | 6/2008 | Freitag .................. A61M 16/16 |
| | | 128/200.26 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0278346 A1 | 11/2011 | Hull et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0253329 A1 | 10/2012 | Zemlok et al. |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153635 A1* | 6/2013 | Hodgkinson .... A61B 17/07207 |
| | | 227/176.1 |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1* | 7/2013 | Olson .................. A61B 17/068 |
| | | 227/180.1 |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1* | 8/2013 | Hessler ................ A61B 17/115 |
| | | 227/175.1 |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0097224 A1* | 4/2014 | Prior .................... A61B 17/105 |
| | | 227/176.1 |
| 2014/0209658 A1* | 7/2014 | Skalla ................ A61B 17/1155 |
| | | 227/175.1 |
| 2014/0222039 A1* | 8/2014 | Khosrovaninejad ...... A61F 2/04 |
| | | 606/151 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2018/0078260 A1* | 3/2018 | Matonick ............ A61B 17/1114 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1588667 A1 | 10/2005 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |
| WO | 2018057324 A1 | 3/2018 |
| WO | 2018140066 A1 | 8/2018 |

* cited by examiner

DEVICE AND METHOD FOR ATTACHMENT OF A STOMAL SLEEVE

CROSS-REFERENCE TO RELATED APPLICATIONS

This application claims the benefit of and priority to U.S. Provisional Patent Application Ser. No. 62/581,059 filed Nov. 3, 2017, the entire disclosure of which is incorporated by reference herein.

BACKGROUND

1. Technical Description

The present disclosure is directed to a device and method for attaching a stomal sleeve to a stoma and, more particularly, to method of attaching a stomal sleeve to a stoma using a circular stapling device.

2. Background of Related Art

During an ostomy procedure, a bisected portion of an intestine is secured to an exterior surface of the abdominal wall to provide internal access into the intestine for collecting fecal matter. The exteriorization of the intestine is called a stoma. Ostomy procedures include ileostomies and colostomies. In an ileostomy procedure, an end of the ileum (i.e., small intestine) is pulled through the abdominal wall and is flared outwardly and sutured to the skin, leaving a smooth, rounded, inside-out ileum as the stoma. In a colostomy procedure, an end or portion of the colon is pulled through the abdominal wall and flared outwardly and fastened (e.g., stitched) to the skin of the patient to form a stoma.

Ostomy surgery is sometimes performed on an emergency basis due to diverticulitis, trauma, radiation complications, volvulus, necrotic bowel, bowel perforation, etc. Children and adults alike may require an ostomy. An ostomy may only be temporary to allow for healing of the bowel or a decrease of inflammation at the surgical site. In some instances an ostomy may be permanent.

Typically, an ostomy bag is secured to the stoma to collect fecal matter from the intestine. If the fecal matter leaks and/or contacts the skin of a patient defining the stoma, the patient's skin can become irritated and/or infected causing the patient pain and discomfort. As such, a need exists for a surgical instrument and method for bypassing an area adjacent the stoma to minimize contact between the patient's skin and fecal matter being collected in the ostomy bag.

SUMMARY

In one aspect of the present disclosure, a stapling device includes a tool assembly having an anvil assembly and a shell assembly. The anvil assembly has an anvil shaft and an anvil head having an annular configuration supported on the anvil shaft. The anvil head defines a first tissue contact surface and includes an annular array of staple deforming pockets positioned about the first tissue contacting surface. The shell assembly has a staple cartridge including a second tissue contact surface having an annular array of staple receiving pockets. The tool assembly is movable from an unapproximated position in which the anvil assembly is spaced from the staple cartridge to an approximated position in which the tissue contacting surfaces of the anvil assembly and the staple cartridge are in closer juxtaposed alignment. A stomal sleeve has a tubular configuration, a first end portion secured to the first tissue contacting surface of the anvil head radially inwardly of the annular array of staple deforming pockets, and a second end portion secured to a distal surface of the anvil head.

In embodiments, the cartridge assembly includes an annular knife that is movable from a retracted position recessed within the staple cartridge to an advanced position in contact with the anvil head.

In some embodiments, in the advanced position of the annular knife, the annular knife is positioned to engage the first end portion of the stomal sleeve.

In certain embodiments, the second end portion of the stomal sleeve is closed.

In embodiments, the first end portion of the stomal sleeve defines an opening.

In some embodiments, the stomal sleeve is formed from a non-degradable, bio-compatible, pliable material.

In certain embodiments, the stomal sleeve is formed from a polymeric material.

In embodiments, the first and second end portions of the stomal sleeve are secured to the anvil head using an adhesive.

In another aspect of the disclosure, a method of attaching a stomal sleeve to a stoma using a circular stapling device includes inserting a tool assembly of the circular stapling device into the stoma with a stomal sleeve attached to an anvil assembly of the tool assembly, wherein the stomal sleeve has a first end portion connected to a first tissue contact surface of the anvil assembly and a second end portion attached to a distal face of an anvil head of the anvil assembly; positioning dermal and intestinal tissue into a tissue gap defined between a staple cartridge of a shell assembly of the tool assembly and the anvil assembly; approximating the shell assembly of the tool assembly with the anvil assembly to clamp the dermal and intestinal tissue between the shell and anvil assemblies; firing the circular stapling device to secure the first end portion of the stomal sleeve to the dermal and intestinal tissue; withdrawing the circular stapling device from the stoma to withdraw a second end portion of the stomal sleeve from the stoma; and disengaging the second end portion of the stomal sleeve from the anvil head of the anvil assembly such that the second end portion of the stomal sleeve is positioned externally of the stoma.

In embodiments, the method includes detaching the stomal sleeve from the tissue contact surface of the anvil assembly.

In embodiments, detaching the stomal sleeve from the tissue contact surface of the anvil is effected by an annular knife of the shell assembly.

In embodiments, the method includes cutting the second end portion of the stomal sleeve to separate the second end portion of the stomal sleeve from the anvil assembly.

BRIEF DESCRIPTION OF THE DRAWINGS

Various embodiments of the presently disclosed stapling device and method for attaching a stomal sleeve to a stoma are described herein below with reference to the drawings, wherein.

DETAILED DESCRIPTION OF EMBODIMENTS

Figure 1:
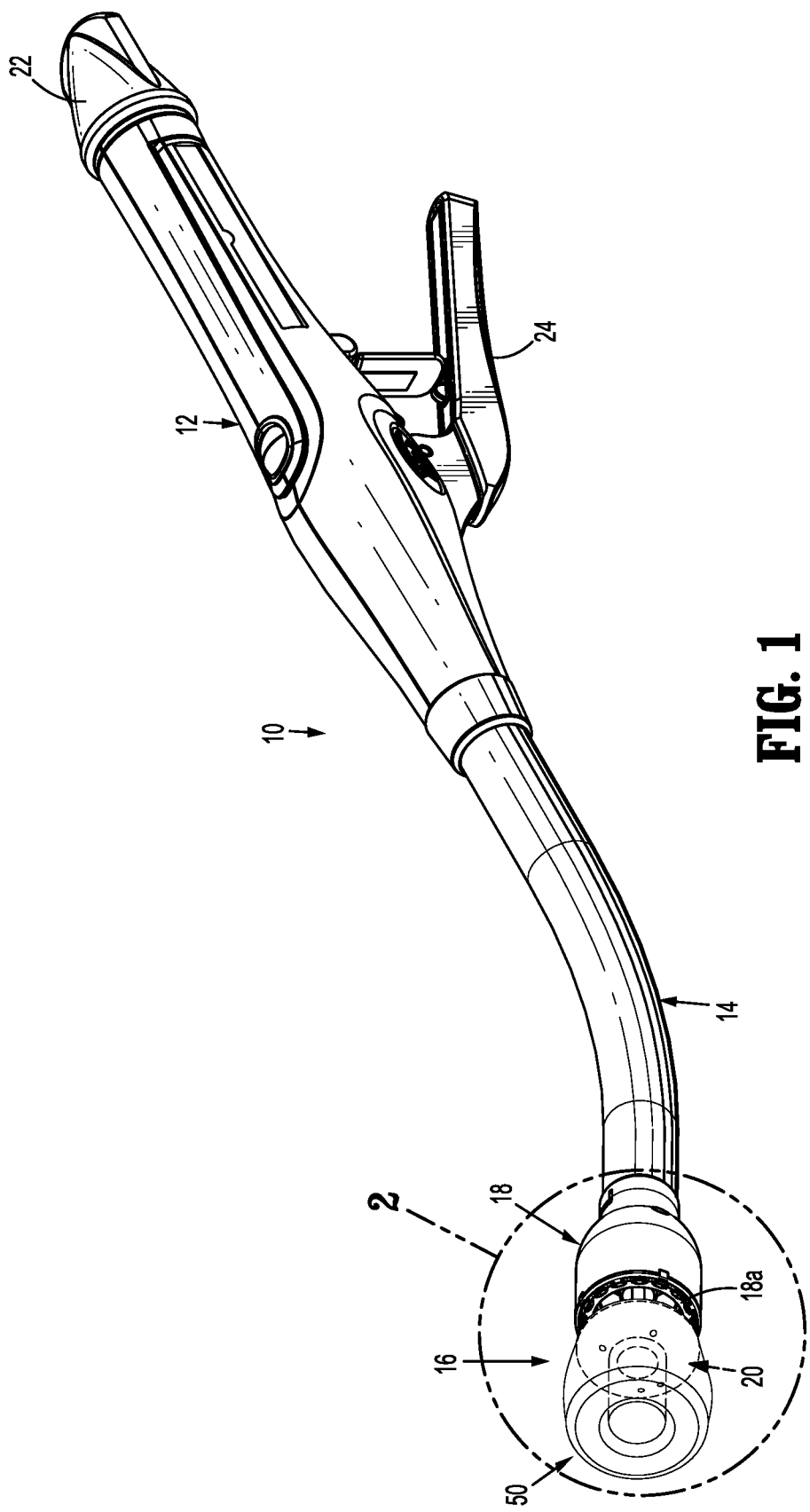
FIG. 1 is a side perspective view of one embodiment of the presently disclosed surgical stapling device supporting a stomal sleeve on an anvil assembly of the stapling device.

The presently disclosed device and method for attaching a stomal sleeve to a stoma will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. In addition, the term clinician is used generally to refer to medical personnel including surgeons, doctors, nurses, and support personnel.

The presently disclosed stapling device has a stomal sleeve secured to an anvil assembly of the stapling device. The stapling device includes a tool assembly having an annular cartridge, an annular anvil assembly that is movable in relation to the annular cartridge between unapproximated and approximated positions, and an annular knife that is moveable into the anvil assembly to cut tissue and disengage one end of the stomal sleeve from attachment with the anvil assembly when the stapling device is fired. The anvil assembly includes an anvil head that defines a tissue contact surface. The stomal sleeve has a tubular configuration having a first end portion secured to the tissue contact surface of the anvil head and a second end portion secured to a distal face of the anvil head.

The presently disclosed method of attaching a stomal sleeve to a stoma includes inserting the tool assembly of the stapling device into the stoma with the stomal sleeve attached to the anvil assembly; positioning dermal and intestinal tissue into a tissue gap defined between the cartridge and anvil assemblies; approximating the cartridge and anvil assemblies to clamp the dermal and intestinal tissue between the cartridge and anvil assemblies; firing the stapling device to secure the first end portion of the stomal sleeve to the dermal and intestinal tissue; withdrawing the stapling device from the stoma to withdraw the second end portion of the stomal sleeve from the stoma; and disengaging the second end portion of the stomal sleeve from the anvil head of the anvil assembly such that the second end portion of the stomal sleeve is positioned externally of the stoma.

Particular embodiments of the present disclosure are described below with reference to the accompanying drawings. However, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to employ the present disclosure in virtually any appropriately detailed structure.

Referring to FIG. 1, the presently disclosed device for attaching a stomal sleeve to a stoma is identified in the figures generally as 10 and includes a handle assembly 12, an elongated body portion 14, and a tool assembly 16. The tool assembly 16 includes an annular shell assembly 18 having an annular staple cartridge 18a and an annular anvil assembly 20 that are movable in relation to each other between an unapproximated or spaced position and an approximated position. The handle assembly 12 includes an approximation knob 22 that is actuable to move the anvil assembly 20 in relation to the cartridge assembly 18 between the spaced and approximated positions to clamp tissue and a firing trigger 24 that is actuable to fire staples 26 (FIG. 3) from the staple cartridge 18a into tissue and to advance an annular knife 28 (FIG. 3) into the anvil assembly 20. For a detailed description of an exemplary stapling device suitable for use for attaching a stomal sleeve to a stoma, see U.S. Pat. No. 7,857,187 ("the '187 patent") which is incorporated herein by reference in its entirety.

Although the presently disclosed stapling device 10 is shown and described as being a manually powered device, it is envisioned that the stapling device 10 can be an electrically powered device such as described in U.S. Patent Publication No. 2012/0253329 which is incorporated herein by reference in its entirety.

Figure 2:
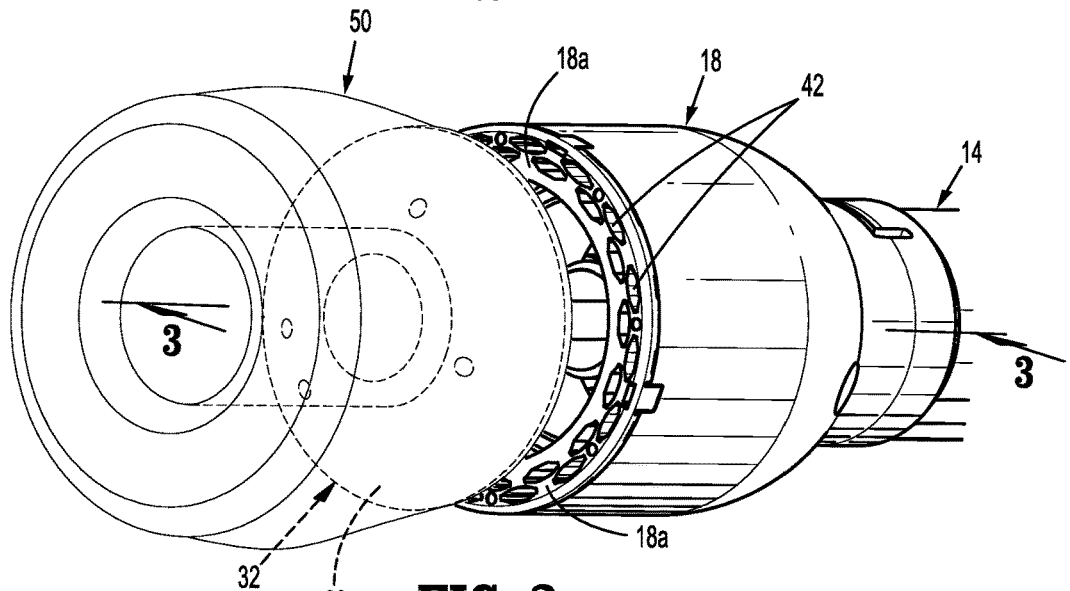
FIG. 2 is an enlarged view of the indicated area of detail shown in FIG. 1.
Figure 3:
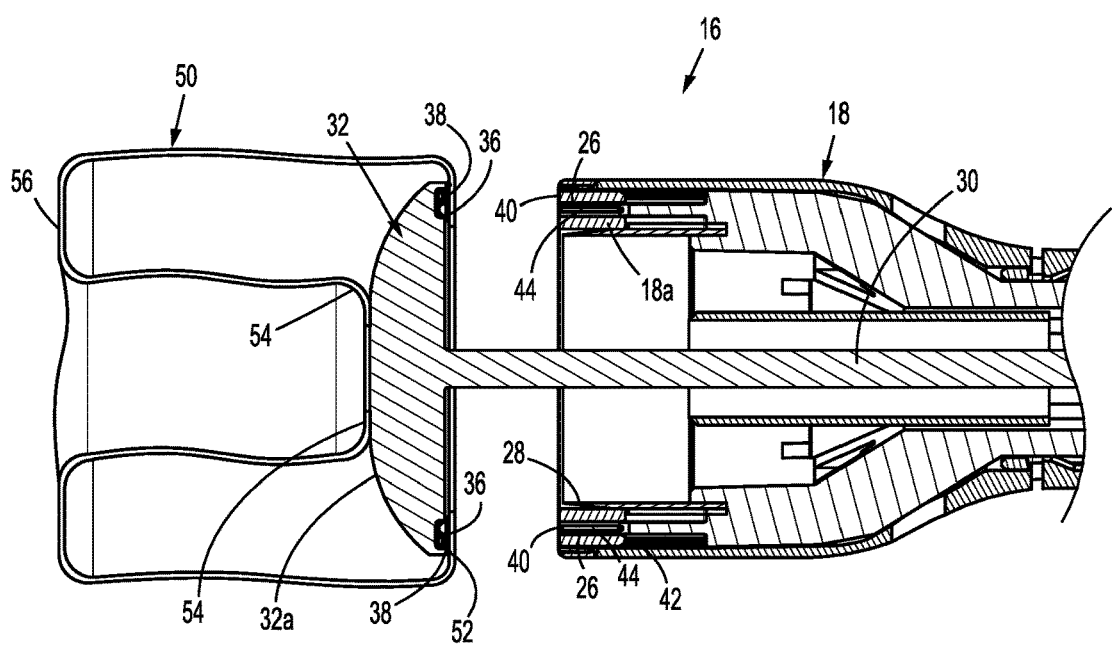
FIG. 3 is a side cross-sectional view taken along section line 3-3 of FIG. 2.

Referring to FIGS. 2 and 3, the anvil assembly 20 includes an anvil shaft 30 (FIG. 3) and an anvil head 32 secured to a distal portion of the anvil shaft 30. The anvil head 32 has a distally facing surface 32a and is attached to a distal portion of the anvil shaft 30 as shown in FIG. 3. Alternatively, the anvil head 32 can be pivotally attached to the distal portion of the anvil shaft 30 such as described in the '187 patent. A proximal end of the anvil shaft 30 is connected to an approximation mechanism of the device 10. The anvil shaft 30 can be fixedly connected to the approximation mechanism of the device 10 as shown, or, in the alternative, the anvil shaft 30 can be removably connected to the approximation mechanism of the device 10, as described in the '187 patent. For a more detailed description of the interconnection between the anvil shaft and the approximation mechanism of the device 10, see the '187 patent.

The anvil head 32 defines a first annular tissue contact surface 36 that includes a plurality of staple deforming pockets 38. The staple deforming pockets 38 (FIG. 3) are disposed in an annular array about the first annular tissue contact surface 36. The staple cartridge 18a includes a second annular tissue contact surface 40 and includes a plurality of staple pockets 42. The staple pockets 42 are positioned in an annular array about the second tissue contact surface 40 and receive staples 44. The cartridge assembly 18 also includes the annular knife 28 that is positioned to engage the anvil head 32 within the annular array of staple deforming pockets 38 when the stapling device is fired as discussed in further detail below. For a more detailed description of the cartridge and anvil assemblies, see the '187 patent.

Figure 3A:
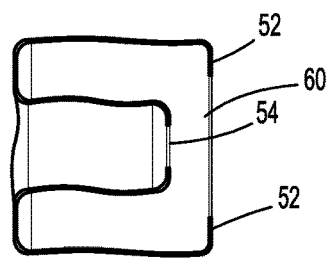
FIG. 3A is a side view of the stomal sleeve of the surgical stapling device of FIG. 1.

The anvil head 32 supports a stomal sleeve 50 that has a tubular configuration and may be formed from a biocompatible, non-degradable, pliable material, e.g., a polymeric material. In embodiments, the stomal sleeve 50 has a first end portion 52 that is secured to the first tissue contact surface 36 of the anvil head 32 at a location radially inwardly of the annular array of staple deforming pockets 38 and a second end portion 54 that is secured to the distally facing surface 32a of the anvil head 32 such that a central portion 56 of the stomal sleeve 50 is positioned distally of the second end portion 54 of the stomal sleeve 50. The end portions 52, 54 of the stomal sleeve can be secured to the anvil head 32 using adhesives or the like. In embodiments, the first end portion 52 of the stomal sleeve 50 defines an opening 60 (FIG. 3A) and the second end portion 54 is closed. It is envisioned that both of the first and second end portions 52, 54 of the stomal sleeve 50 can initially define an opening or be closed.

Figure 4:
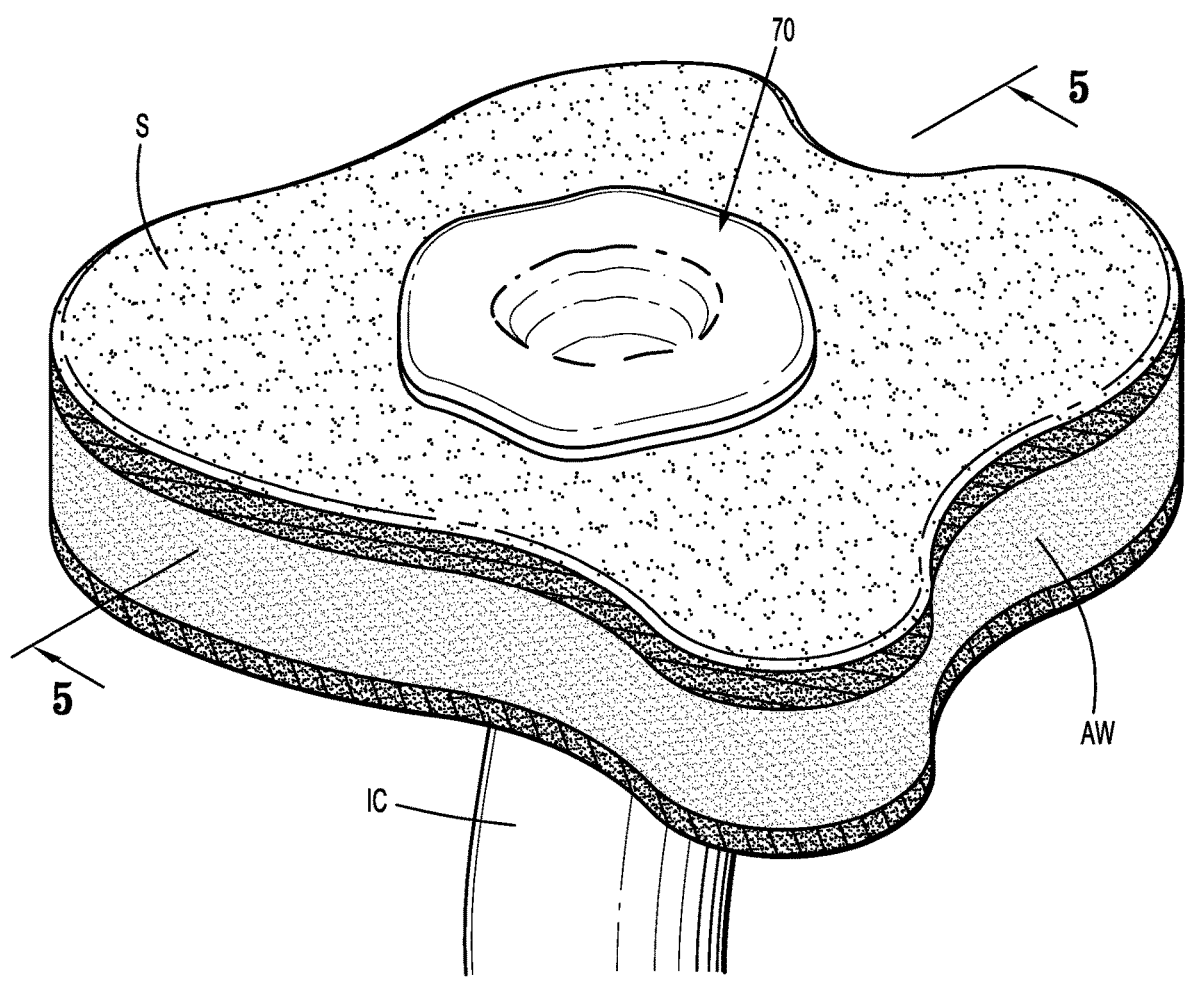
FIG. 4 is a side perspective view of a stoma of a bowel extending through an opening in an abdomen of a patient.
Figure 5:
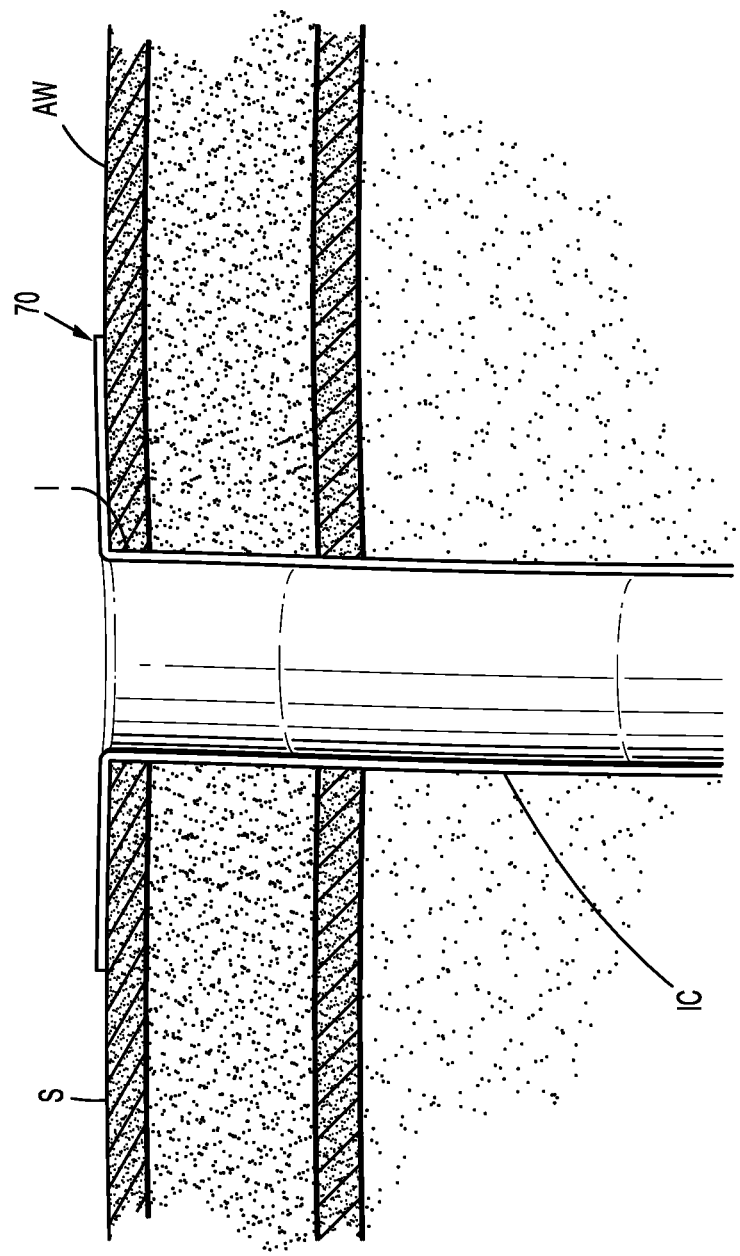
FIG. 5 is a cross-sectional view taken along section line 5-5 of FIG. 4.

Referring to FIGS. 4 and 5, during formation of a stoma 70, a vessel portion, e.g., small or large intestine or colon "IC", is pulled through an incision "I" (FIG. 5) in the abdominal wall "AW" and is everted outwardly and secured to an outer surface of the skin "S", leaving a smooth, rounded, everted vessel portion as the stoma 70. An ostomy bag (not shown) is secured to the stoma 70 to direct fecal matter from within the vessel portion "IC" into the ostomy bag. Formation of the stoma can be performed using a variety of techniques and devices and does not form part of the presently disclosed method. Embodiments of a stapling device and method for forming a stoma are described in U.S. application Ser. No. [203-11280] which is incorporated herein in its entirety by reference.

Figure 6:
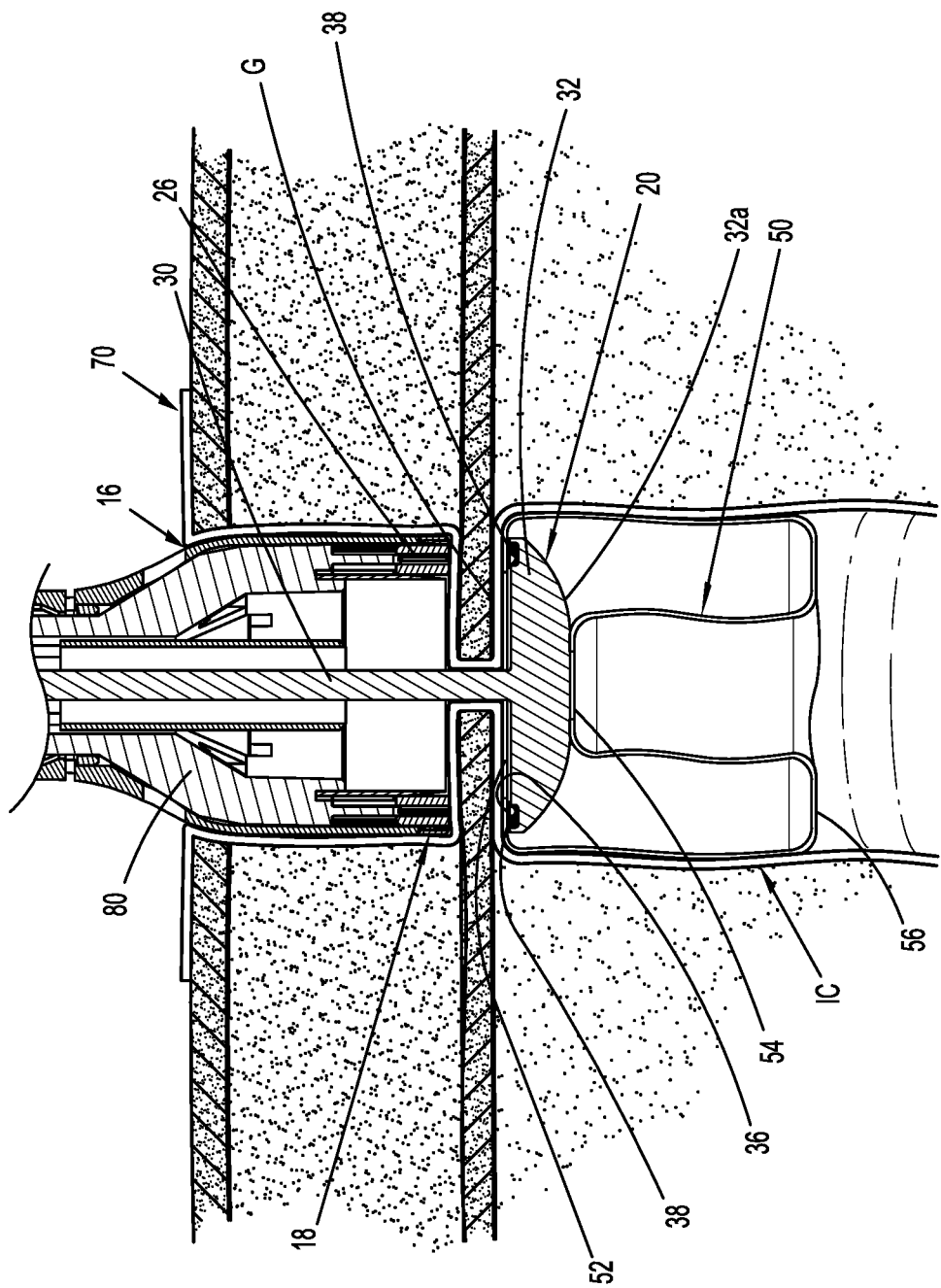
FIG. 6 is a side cross-sectional view of the surgical stapling device of FIG. 1 inserted into the stoma of FIG. 5 prior to full approximation of the stapling device with the stomal sleeve extending from the anvil assembly into the intestine/colon of the patient.

Referring to FIG. 6, after the stoma 70 is created, in order to attach the stomal sleeve 50 to a position within the vessel portion "IC", the tool assembly 16 of the stapling device 10 is inserted through the stoma 70 with the cartridge assembly 18 and anvil assembly 20 in an unapproximated position. In this position, the stomal sleeve 50 is supported on the anvil head 32 and extends into the vessel portion "IC" distally of the anvil head 32. With the tool assembly 16 positioned within the vessel portion "IC", tissue including a portion of the vessel portion "IC" is drawn into the tissue into tissue gap "G" defined between the staple cartridge 18a and the anvil assembly 20. As discussed above, the stomal sleeve 50 has a first end portion 52 that is secured to the first tissue contact surface 36 of the anvil head 32 at a location radially inwardly of the annular array of staple deforming pockets 38 and a second end portion 54 that is secured to a distal face 32a of the anvil head 32.

Figure 7:
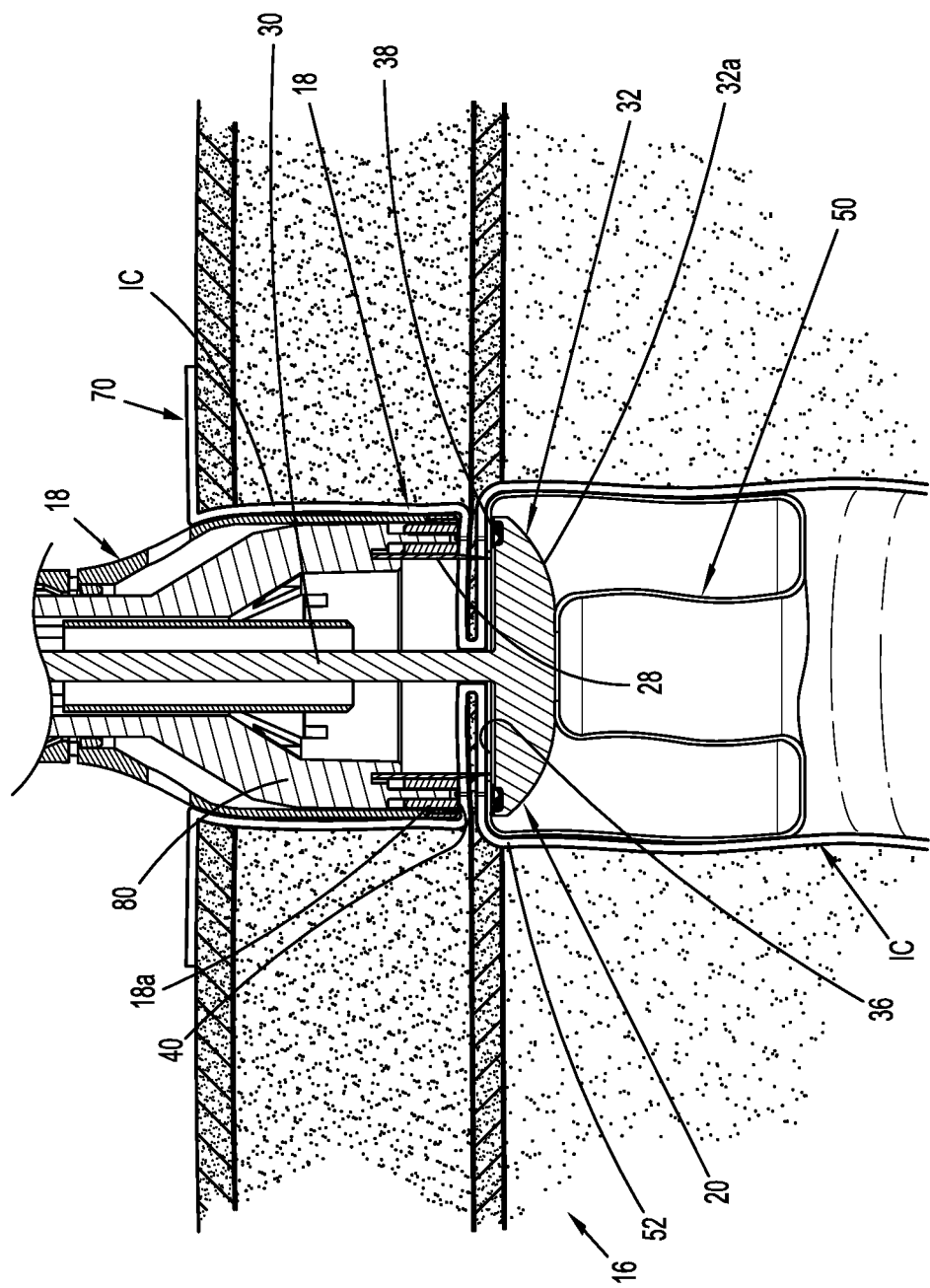
FIG. 7 is side cross-sectional view of the surgical stapling device of FIG. 1 inserted into the stoma of FIG. 5 with the stapling device in an approximated and fired condition and the stomal sleeve extending from the anvil assembly into the intestine/colon of the patient.

Referring to FIG. 7, after tissue has been drawn into the tissue gap "G" (FIG. 6), the stapling device 10 is approximated to clamp tissue between the cartridge assembly 18 and the anvil assembly 20. More specifically, when the tool assembly 16 is moved to the approximated position, tissue including a portion of the vessel portion "IC" is clamped between the tissue contact surface 36 of the anvil head 32 and the tissue contact surface 40 of the staple cartridge assembly 18a. As shown, the first end portion 52 of the stomal sleeve 50 is also clamped between the tissue and the contact surface 36 of the anvil head 32.

When the stapling device 10 (FIG. 1) is fired, a pusher 80 of the stapling device 10 is advanced through the cartridge assembly 18 to drive staples 26 (FIG. 6) from the staple cartridge 18a through the tissue including the vessel portion "IC". Simultaneously, the annular knife 28 is advanced towards the anvil head 32 to cut the tissue and the first end portion 52 of the stomal sleeve 50 radially inwardly of the staple deforming pockets 38. When the annular knife 28 cuts through the first end portion 52 of the stomal sleeve 50, the first end portion 52 of the stomal sleeve 50 is separated from the anvil head 32 and stapled to the vessel portion "IC" and surrounding tissue (FIG. 8).

Figure 8:
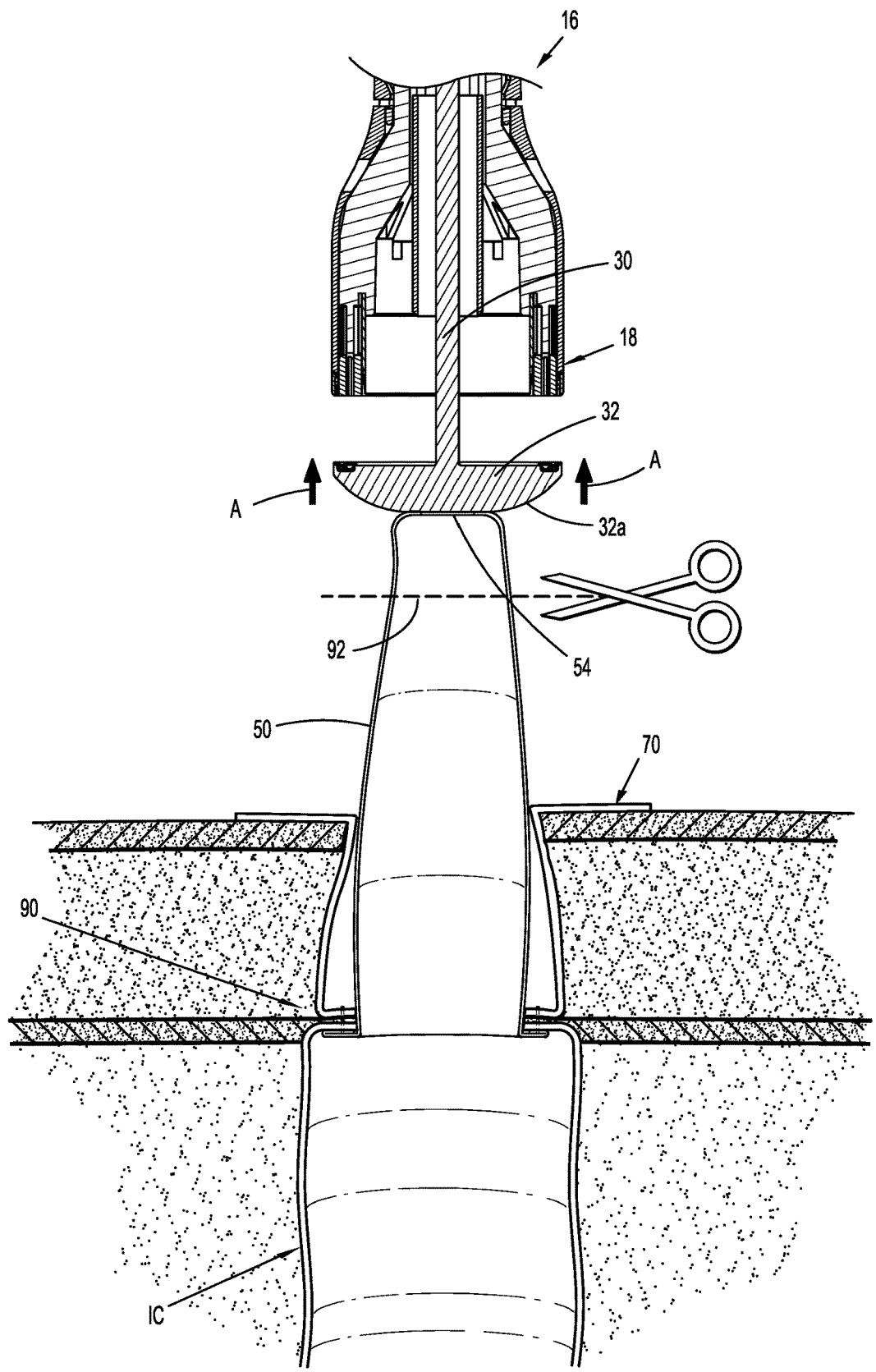
FIG. 8 is side cross-sectional view of the surgical stapling device of FIG. 1 as the stapling device is withdrawn from the stoma of FIG. 7 after the stapling device is fired with the stomal sleeve attached to the anvil assembly and extending from the stoma of the patient.

Referring to FIG. 8, after the tool assembly 16 of the stapling device 10 is unapproximated to release the clamped tissue from between the cartridge assembly 18 and the anvil assembly 20, the stapling device 10 (FIG. 1) can be withdrawn in the direction indicated by arrows "A" in FIG. 8 to withdraw the tool assembly 16 from the stoma 70. As discussed above, the second end portion 54 of the stomal sleeve 50 is attached to the distal face 32a of the anvil head 32. Thus, as the tool assembly 16 is withdrawn from the stoma 70, the second end portion 54 of the stomal sleeve 50 is pulled through the stoma 70 to a position externally of the stoma 70 such that the stomal sleeve 50 defines an internal liner from the stapling location 90 within the vessel portion "IC" through the stoma 70.

Figure 9:
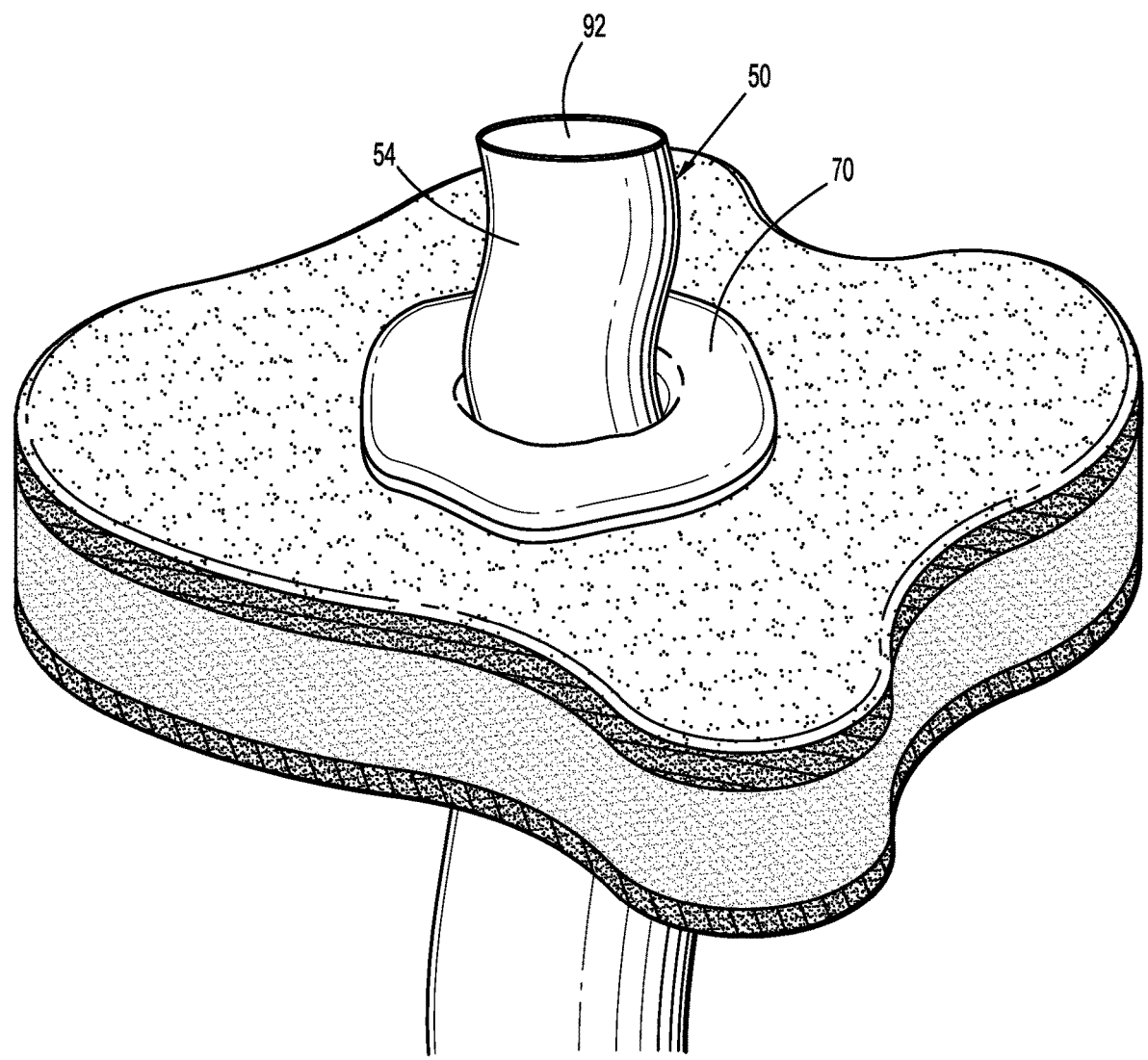
FIG. 9 is a side perspective view of the stomal sleeve extending from the stoma of the patient after the stomal sleeve is cut and separated from the anvil assembly.

Referring also to FIG. 10, when the stomal sleeve 50 is positioned externally of the stoma 50, the second end portion 54 of the stomal sleeve 50 can be separated from the anvil head 32 to define an opening or mouth 92 adjacent the second end portion 54 of the stomal sleeve 50. In embodiments, the second end portion 54 of the stomal sleeve 50 is closed and is separated from the anvil head 32 by cutting the second end portion 54 using a scissor 96 (FIG. 9) along a cut line "CL". As illustrated, in this position, the stomal sleeve 50 provides an insulative barrier from a position within the vessel portion "IC" through the stoma 70. It is also envisioned that the second end portion 54 of the stomal sleeve 50 may define an opening and be secured to the anvil head 32 by an adhesive. In this embodiment, instead of cutting the second end portion 54 of the stomal sleeve 50, the second end portion 54 of the stomal sleeve 50 can be separated from the distal surface 32a of the anvil head 32 by pulling the second end portion 54 in a direction away from the anvil head 32 to disengage the second end portion 54 from the adhesive on the anvil head 32. Other methods of releasably securing the second end portion 54 of the stomal sleeve 50 to the anvil head 32 are envisioned.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:
1. A stapling device comprising;
a tool assembly including an anvil assembly and a shell assembly, the anvil assembly having an anvil shaft and an anvil head having an annular configuration supported on the anvil shaft, the anvil head defining a first tissue contact surface and including an annular array of staple deforming pockets positioned about the first tissue contacting surface, the shell assembly including a staple cartridge defining a second tissue contact surface having an annular array of staple receiving pockets, the tool assembly being movable from an unapproximated position in which the anvil assembly is spaced from the staple cartridge to an approximated position in which the tissue contacting surfaces of the anvil assembly and the staple cartridge are in closer juxtaposed alignment; and a stomal sleeve having a tubular configuration, the stomal sleeve having a first end portion secured to the first tissue contacting surface of the anvil head radially inwardly of the annular array of staple deforming pockets with a first adhesive and a second end portion secured to a distal surface of the anvil head with a second adhesive.

2. The stapling device of claim 1, wherein the shell assembly includes an annular knife that is movable from a retracted position recessed within the staple cartridge to an advanced position in contact with the anvil head.

3. The stapling device of claim 2, wherein in the advanced position of the annular knife, the annular knife is positioned to engage the stomal sleeve at a location adjacent the first end portion.

4. The stapling device of claim 3, wherein the second end portion of the stomal sleeve is closed.

5. The stapling device of claim 4, wherein the first end portion of the stomal sleeve defines an opening.

6. The stapling device of claim 3, wherein the stomal sleeve is formed from a non-degradable, bio-compatible, pliable material.

7. The stapling device of claim 5, wherein the stomal sleeve is formed from a polymeric material.

* * * * *